(12) United States Patent
VanRavenhorst-Bell et al.

(10) Patent No.: US 12,097,045 B2
(45) Date of Patent: Sep. 24, 2024

(54) SLIP-RESISTANCE PATCH FOR ORAL DEVICES

(71) Applicant: Wichita State University, Wichita, KS (US)

(72) Inventors: Heidi A. VanRavenhorst-Bell, Wichita, KS (US); Jeremy Patterson, Wichita, KS (US)

(73) Assignee: WICHITA STATE UNIVERSITY, Wichita, KS (US)

( * ) Notice: Subject to any disclaimer, the term of this patent is extended or adjusted under 35 U.S.C. 154(b) by 980 days.

(21) Appl. No.: 17/098,532

(22) Filed: Nov. 16, 2020

(65) Prior Publication Data

US 2021/0169416 A1    Jun. 10, 2021

Related U.S. Application Data

(60) Provisional application No. 62/936,098, filed on Nov. 15, 2019.

(51) Int. Cl.
*A61B 5/22* (2006.01)
*A61B 5/00* (2006.01)
*A61B 13/00* (2006.01)

(52) U.S. Cl.
CPC .............. *A61B 5/683* (2013.01); *A61B 5/224* (2013.01); *A61B 5/682* (2013.01); *A61B 13/00* (2013.01); *A61B 5/4552* (2013.01)

(58) Field of Classification Search
CPC ......... A61B 5/224; A61B 5/228; A61B 5/682; A61B 5/4542–4557; A61B 13/00; A61F 5/56–58
See application file for complete search history.

(56) References Cited

PUBLICATIONS

Solomon et al., "Assessment of Orofacial Strength in Patients with Dysarthria," J Med Speech Lang Pathol. Dec. 1, 2008; 16(4): 251-258. (Year: 2008).*
Youmans et al., "Measures of tongue function related to normal swallowing", Dysphagia, 21(2), p. 102-11, Apr. 2006.
Robbins et al., "The effects of lingual exercise in stroke patients with dysphagia", Archives of Physical Medicine and Rehabilitation, 88(2), p. 150-158, Feb. 2007.
Hewitt et al., "Standardized Instrument for Lingual Pressure Measurement", Dysphagia, (1), 16-25, Apr. 2008.

(Continued)

*Primary Examiner* — Thaddeus B Cox
(74) *Attorney, Agent, or Firm* — Stinson LLP (57) ABSTRACT

The present disclosure provides a slip-resistant patch for a tongue bulb that includes a perimeter portion and a planar body. The perimeter portion defines a shape and size of the slip-resistant patch while the planar body is defined by the perimeter portion of the slip-resistant patch. The planar body is configured to contour to a surface of a tongue bulb. The planar body includes a first major surface and an opposing second major surface. The first major surface includes a textured material while the second major surface includes an adhesive material. The textured material is configured to be positioned on a surface of an oral cavity and maintain position on the surface of the oral cavity throughout lingual movement within the oral cavity. The adhesive material is of a pressure sensitive material and is configured to adhere to the surface of the tongue bulb.

14 Claims, 7 Drawing Sheets

(56) References Cited

PUBLICATIONS

Neel et al., "Can IOPI be used to measure tongue pressure for speech sounds?", Journal of Medical Speech-Language Pathology, 16(4), 235.

Yoshikawa et al., Comparison of Three Types of Tongue Pressure Measurement Devices:, Dysphagia, (3), 6 pages, Jul. 11, 2010.

Adams et al., "A Systematic Review and Meta-analysis of Measurements of Tongue and Hand Strength and Endurance Using the Iowa Oral Performance Instrument (IOPI)", Dysphagia, 28, 350-369, Mar. 7, 2013.

Ray et a;., "Enhancing Swallowing Functions with IOPI: A Case Report", Archives of Physical Medicine and Rehabilitation, (10). Retrieved on Nov. 19, 2021 from https://www.archives-pmr.org/action/showPdf?pii=S0003-9993%2816%2930870-X.

Villa et al., "Can myofunctional therapy increase tongue tone and reduce symptoms in children with sleep-disordered breathing?" Sleep & Breathing, 21(4), 1025-1032, Mar. 18, 2017.

Keskool et al, "The Relationships among Objective Measures of Tongue Strength and Risk of Aspiration", Siriraj Medical Journal, 70(4), 302-309.(2018).

Pitts et al., "Lingual Pressure as a Clinical Indicator of Swallowing Function in Parkinson's Disease", Journal of Speech, Language & Hearing Research, 61(2), 257-265.(2018).

Park et al., "Effect of tongue strength training using the Iowa Oral Performance Instrument in stroke patients with dysphagia", Journal of Physical Therapy Science, 27(12), 3631-3634, Aug. 2015.

Temple, "OPI Products—IOPI Medical", Retrieved on Nov. 19, 2021 from https://iopimedica..com.

Hart, T. [IOPI Medical]. (Nov. 11, 2013). IOPI Demo Video. Retrieved on Mar. 25, 2019 from https://www.youtube.com/watch?v=PvANJ2XHp0E&t=685s.

Adams et al., "Reliability of measurements of tongue and hand strength and endurance using the Iowa Oral Performance Instrument with healthy adults", Dysphagia, 29(1), 83-95, Sep. 18, 2013.

* cited by examiner

SLIP-RESISTANCE PATCH FOR ORAL DEVICES

CROSS-REFERENCE TO RELATED APPLICATIONS

This application claims priority to U.S. Provisional patent Application Ser. No. 62/936,098, filed Nov. 15, 2019, which is hereby incorporated by reference in its entirety.

FIELD

The present disclosure generally relates to a slip-resistance patch for oral devices that can maintain contact with a surface within an oral cavity.

BACKGROUND

Embodiments of the present disclosure generally relate to oral devices positioned within an oral cavity. The oral cavity commonly refers to a human mouth and all parts of the month such as lips, a tongue, teeth, a mouth roof, and a mouth floor. Oral devices are used for a number of applications that can include, but are not limited to, evaluative, diagnostic, therapeutic, and assistive applications. These devices are designed to be placed inside the oral cavity or in contact with at least portion of the oral cavity. Oral devices in the present art, are often made out of materials that are antibacterial, and depending upon the application, are hard structures, durable, resilient, or sturdy. Familiar examples can include plastics or silicon rubbers. When these materials are placed in an oral cavity, which is a salivated and wet environment, issues and challenges arise if the oral device is not fixated, secured, or otherwise anchored in an intended or optimal position. Without having the oral device secured, the oral device often slips from the intended position, hindering the oral device's ability to be properly used for its intended purpose or application. For example, an oral device used for assessing lingual function, such as tongue strength and tongue endurance, is an Iowa Oral Performance Instrument (IOPI). The IOPI is a smooth plastic, air-filled pressure lingual bulb, commonly known as a tongue bulb, which is placed in a standardized position on a patient's tongue within an oral cavity of the patient. The standardized position is 10-mm from a distal tip of the tongue of the patient for anterior tongue performance measures or 10-mm anterior to the patient's circumvallate papillae for posterior tongue performance measures. The IOPI has been found to have issues regarding slippage from the standardized position, which reduces precision and reliability of measurements recorded during the assessment. Therein, this creates concern to those in the art that measurements from oral devices are inconsistent, unreliable, and can lead to an increased risk of inaccurately evaluating, diagnosing, rehabilitating, and/or preventing lingual disorders, in addition to potentially imposing on one's quality of life. In general, tongue muscle performance has shown to decline as an individual ages, causing the individual's risk of an orofacial myofunctional disorder such as dysphagia and sleep apnea to increase. With use of therapeutic work for lingual function, tongue muscle performance can be restored; however, many insurance companies have required an assessment of lingual function, typically by the IOPI assessment, prior to assisting in cost associated with therapeutic work to validate that the work is necessary. Therefore, a reliable and objective assessment of lingual function is important because without a healthy tongue strength and endurance, the individual may have difficultly performing daily functional tasks such as swallowing, articulation, and maintaining an open upper airway. Therefore, there is a need for a simple and cost-effective solution to reduce oral device slippage from its intended position.

BRIEF SUMMARY

In one aspect, a slip-resistant patch for a tongue bulb comprises a perimeter portion. The perimeter portion defines a shape and size of the slip-resistant patch. A planar body is defined by the perimeter portion of the slip-resistant patch. The planar body is configured to contour to a surface of the tongue bulb. The planar body comprises a first major surface and an opposing second major surface. The first major surface comprises a textured material and the second major surface comprises an adhesive material. The textured material is configured to be positioned on a surface of an oral cavity and maintain position on the surface of the oral cavity throughout lingual movement within the oral cavity. The adhesive material is of a pressure sensitive material and configured to adhere to the surface of the tongue bulb.

In another aspect, a method to reduce slippage of a tongue bulb comprises providing at least one slip-resistant patch including a textured material and an adhesive material. The textured material comprises a textured surface and the adhesive material comprises an adhesive surface on an opposing face of the patch. The adhesive material is at least a portion of a pressure sensitive material. The adhesive surface is adhered to at least one surface of the tongue bulb, creating a texturized tongue bulb. The texturized tongue bulb is placed in contact with at least one surface of a patient's oral cavity.

Other aspects and features will be apparent hereinafter.

BRIEF DESCRIPTION OF DRAWINGS

For a better understanding of the nature and objects of the disclosure, reference should be made to the following detailed description taken in conjunction with the accompanying drawings, in which.

Reference is made in the following detailed description of preferred embodiments to accompanying drawings, which form a part hereof, wherein like numerals may designate like parts throughout that are corresponding and/or analogous. It will be appreciated that the figures have not necessarily been drawn to scale, such as for simplicity and/or clarity of illustration. For example, dimensions of some aspects may be exaggerated relative to others. Further, it is to be understood that other embodiments may be utilized. Furthermore, structural and/or other changes may be made without departing from claimed subject matter. References throughout this specification to "claimed subject matter" refer to subject matter intended to be covered by one or more claims, or any portion thereof, and are not necessarily intended to refer to a complete claim set, to a particular combination of claim sets (e.g., method claims, apparatus claims, etc.), or to a particular claim.

DETAILED DESCRIPTION

Figure 1:
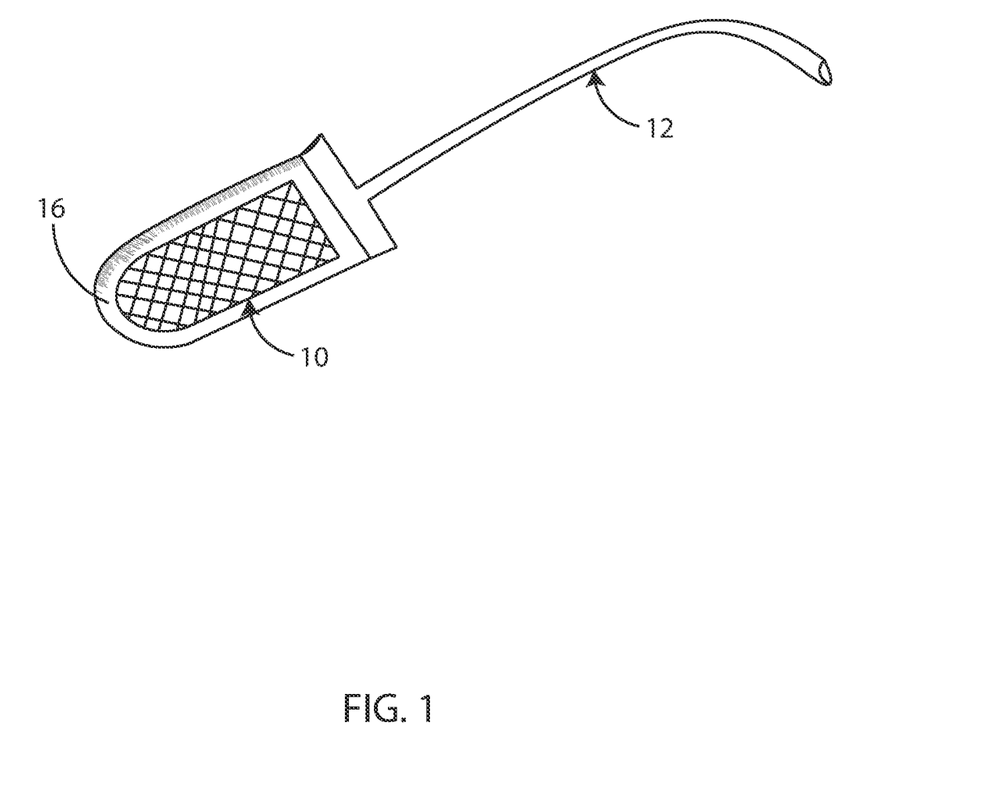
FIG. 1 is an illustration of a slip-resistant patch on a tongue bulb of an Iowa Oral Performance Instrument, forming a texturized oral device.
Figure 2:
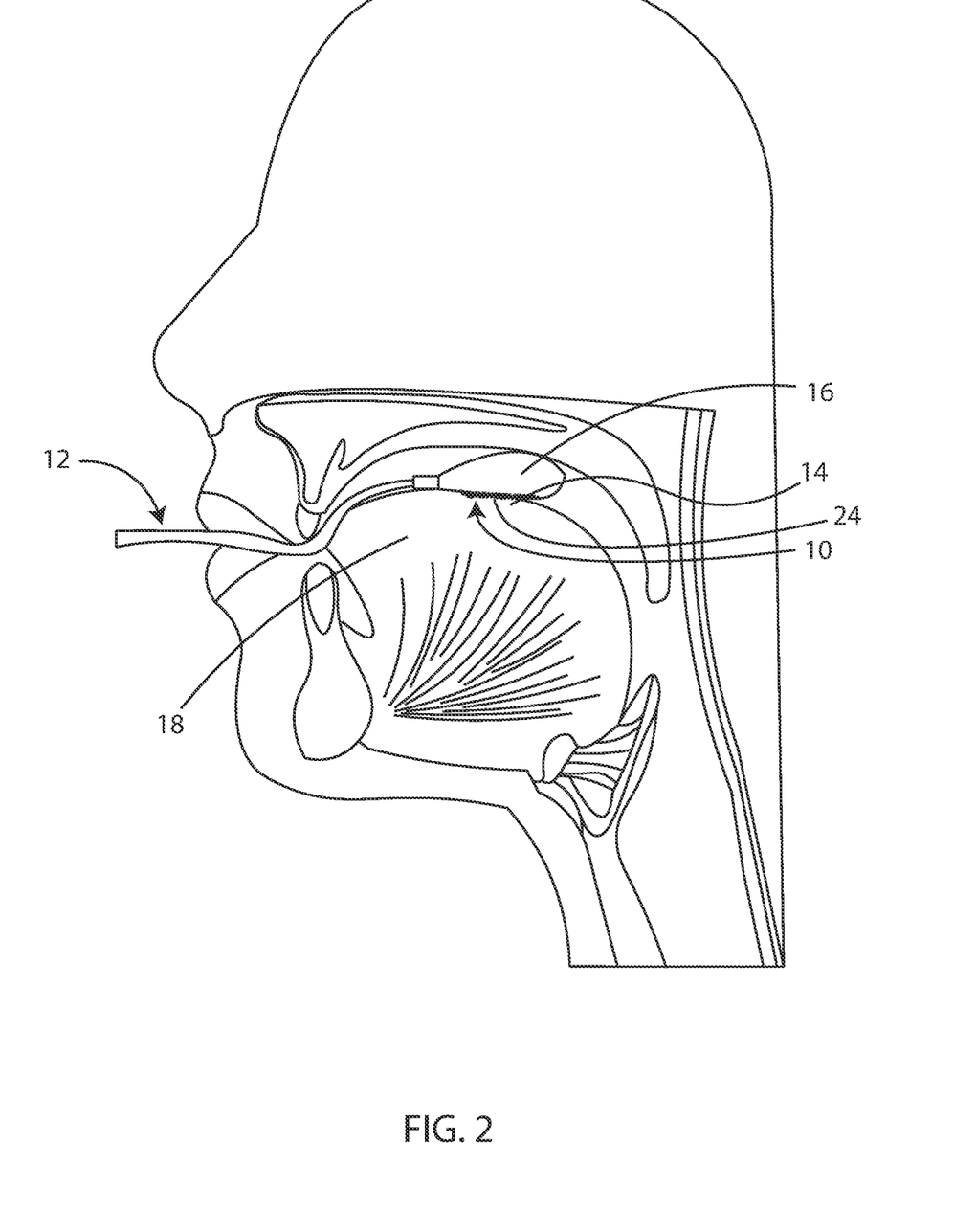
FIG. 2 is an illustration of the texturized oral device positioned within a patient's oral cavity.

The present disclosure provides a slip-resistant patch 10 that is a cost-effective for retrofitting and modifying an existing oral device 12 to ensure the existing oral device can maintain in an intended position 14 or placement inside a patient's oral cavity, as best shown in FIGS. 1-2. The resulting combination of the slip-resistant patch 10 adhering to a surface of the existing oral device 12 creates a texturized oral device. For example, as shown in FIG. 1, a slip-resistant patch 10 can be designed for an existing oral device 12 such as, but not limiting to, a tongue bulb 16 of an Iowa Oral Performance Instrument (IOPI) for a purpose of evaluating a patient for tongue strength and endurance. The slip-resistant patch 10 adheres to a surface of the tongue bulb 16 and provides slip-resistant contact with a surface of a patient's oral cavity, such as but not limiting to, the patient's tongue 18. The slip-resistant patch 10 allows additional control of the tongue bulb 16 during an evaluation. The additional control reduces or minimizes slippage about the tongue during the evaluation by maintaining placement or positioning of the tongue bulb 16 when placed at the intended position 14 on the tongue 18 such that the tongue can perform lingual movement and a static hold while the tongue bulb maintains generally at the intended position, as best shown in FIG. 2. Based off the lingual movement and the static hold, the IOPI measures an amount of pressure (kPa) the tongue 18 produces and maintains on the tongue bulb 16 for correlating to tongue strength and endurance, respectively. By stabilizing the tongue bulb 16 at the intended position 14, reliability of the amount of pressure produced, indicating lingual function, during evaluation increases. Oral assessments of tongue strength and endurance are performed in both anterior and posterior regions of the tongue for identifying the patient's risk of orofacial myofunctional disorders such as dysphagia and sleep apnea. As one with skill in the art would understand, the intended position 14 is generally 10-mm from a distal tip of the tongue 18 of the patient for anterior tongue performance and generally 10-mm anterior to the patient's circumvallate papillae for posterior tongue performance.

Figure 3:
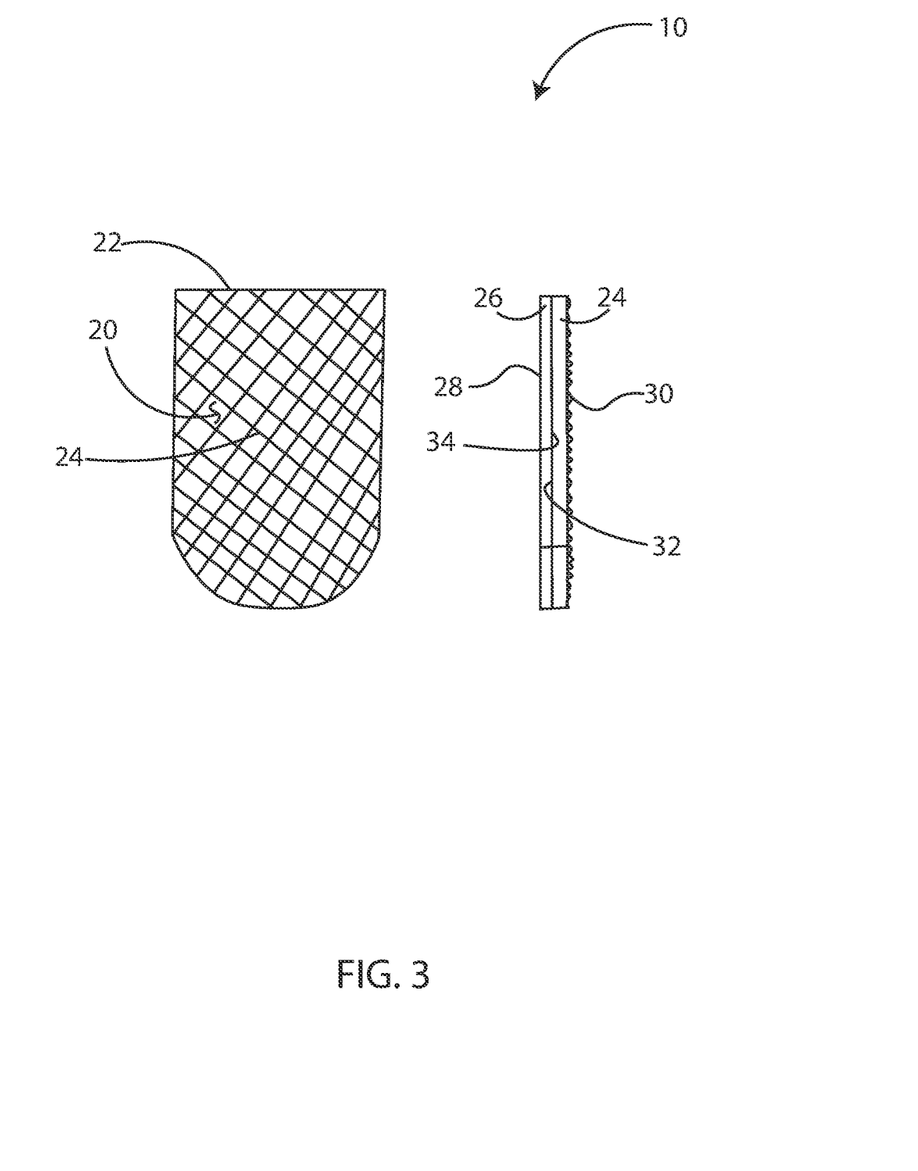
FIG. 3 is an illustration of a top view and side view of the slip-resistant patch.

As shown in FIG. 3, in the preferred embodiment of the present disclosure, a slip-resistant patch 10 comprises a substantially planar body 20, a perimeter portion 22, a textured material 24, and an adhesive material 26. The planar body 20 is defined by the perimeter portion 22, a first major surface 28, and an opposing second major surface 30. As shown, the first major surface 28 of the slip-resistant patch 10 includes the textured material 24 while the other second major surface 30 includes the adhesive material 26. The first major surface 28 and the second major surface 30 can adjoin by, for example but not limiting to, an adhesive layer formed across a backside 32 of the textured material 24 or a backside 34 of the adhesive material 26 such that the backsides affix. The adhesive layer can be any adhesive with an ability to securely adhere the backside 32 of the textured material 24 to the backside 34 of the adhesive material 26 and maintain adhesion when the slip-resistant patch 10 is within an oral cavity.

Figure 4:
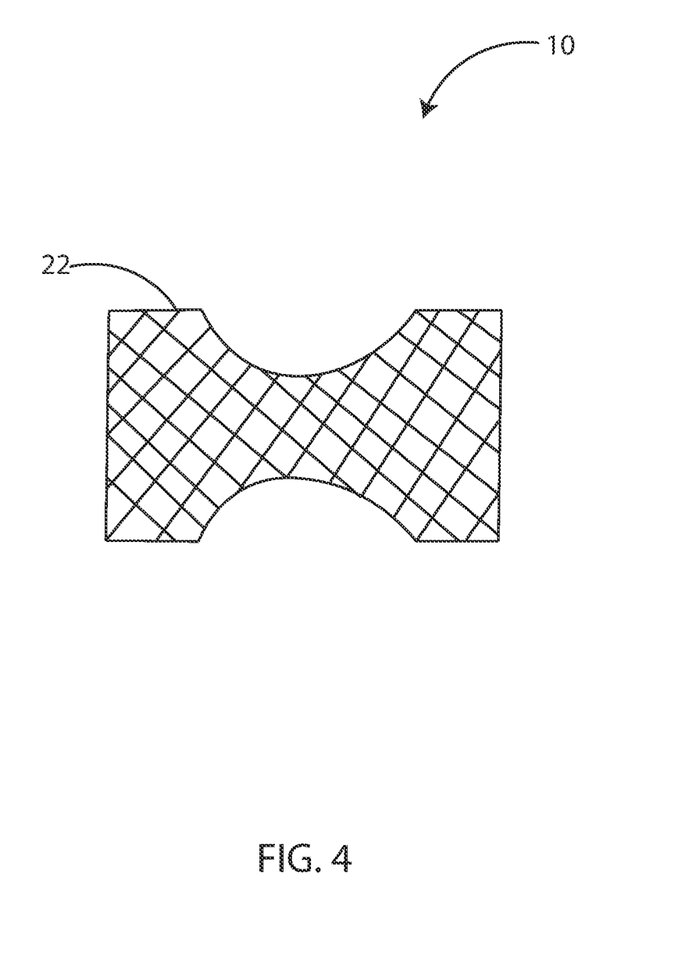
FIG. 4 is an alternative embodiment of the slip-resistant patch.

The perimeter portion 22 of the slip-resistant patch 10 defines geometry or shape of the slip-resistant patch, as best shown in FIGS. 3-4. The shape of the slip-resistant patch 10 is configured to be representative of a surface area on the existing oral device 12 to which the slip-resistant patch is to be applied, and can therefore have a plurality of mixed geometries such as a portion or combination of circular, oblong, square, rectangular, and pentagonal, hexagonal shapes. As can be appreciated, the size of the slip-resistant patch 10 can vary significantly as the size and shape is dependent on the surface area of the existing oral device 12 to which the slip-resistant patch is to be applied. In one or more aspects, the slip-resistant patch 10 is generally sized and shaped to cover at least half of at least one surface of the existing oral device in contact with an oral cavity, as best shown in FIG. 1. As one will skill in the art would appreciate, the slip-resistant patch 10 is meant to reduce slippage and therefore can be applied to any surface of an oral device in contact with a surface of an oral cavity. The slip-resistant patch 10 can be applied to a at least one surface of a patient's oral cavity, for example but not limiting to, a tongue, lips, a hard palate, cheeks, gums, teeth, a month roof, and a mouth floor. In following aspect, at least one texturized surface of the textured material 24 is in contact with at least one surface of the patient's oral cavity, as shown in FIG. 2. The shape of the slip-resistant patch 10 can further represent a surface area of the surface of the oral cavity. For example, the shape of the slip-resistant patch 10 can be sized and shaped to fit the underlying oral device, such as the tongue bulb 16, and/or can be configured to fit in the patient's mouth adjacent the patient's tongue (e.g. generally elongated body with a rectangular shape at one end and rounded at the other end), as best shown in FIG. 3.

The textured material 24, as best shown in FIGS. 1-3, is used to reduce the slippage of the tongue bulb 16 when inside an oral cavity, ensuring and maintaining placement at the intended position 14. Therefore, the textured material 24 can be any material with enough surface texture to reduce slippage, particularly as in the preferred embodiment when placed in contact with the patient's tongue 18, as shown in FIG. 2. In addition, the textured material 24 provides a non-abrasive surface during contact, making the material biocompatible. Preferably, a material selected for the textured material 24 is textured and non-abrasive so that the slip-resistant patch 10 does not result in any non-biocompatible effects to a patient or their oral cavity, including irritate, damage, harm, injure, hurt, infect, or wound. Further, in the preferred embodiment, the textured material 24 is porous and has minimal absorbency to avoid collecting and retaining too much saliva from the patient's mouth while within the oral cavity. In one embodiment, the textured surface comprises at least one material selected from fabric, cloth, and/or fiber. Woven fabrics and nonwoven fabrics made of thermoplastic elastomers are known in the art and can be used within the scope of the present disclosure, including for example, polystyrene-type elastomers such as a styrene-isoprenestyrene type block copolymer and hydrogenated block copolymers hydrogenating said block copolymer, polyurethanes, polyesters and polyolefins such as polyethylene, as disclosed. Natural material fibers, fabrics, or cloths can also be used, such as cotton, cellulose, and the like. Further, thin-film materials can be used, such as medical tapes, so long as they have adequate textured surfaces. The materials can be of synthetic or natural origins, or any combination of the listed materials thereof. In one or more embodiments, the slip-resistant patch 10 comprises a substantially planar fabric, cloth, or fiber woven or nonwoven web or mat (or thin film) and a layer of adhesive adjacent at least one major surface of the web or mat (or thin film), such that the texture of the fabric, cloth, or fiber of the first major surface 28 corresponds to the textured material 24 of the slip-resistant patch.

Figure 5:
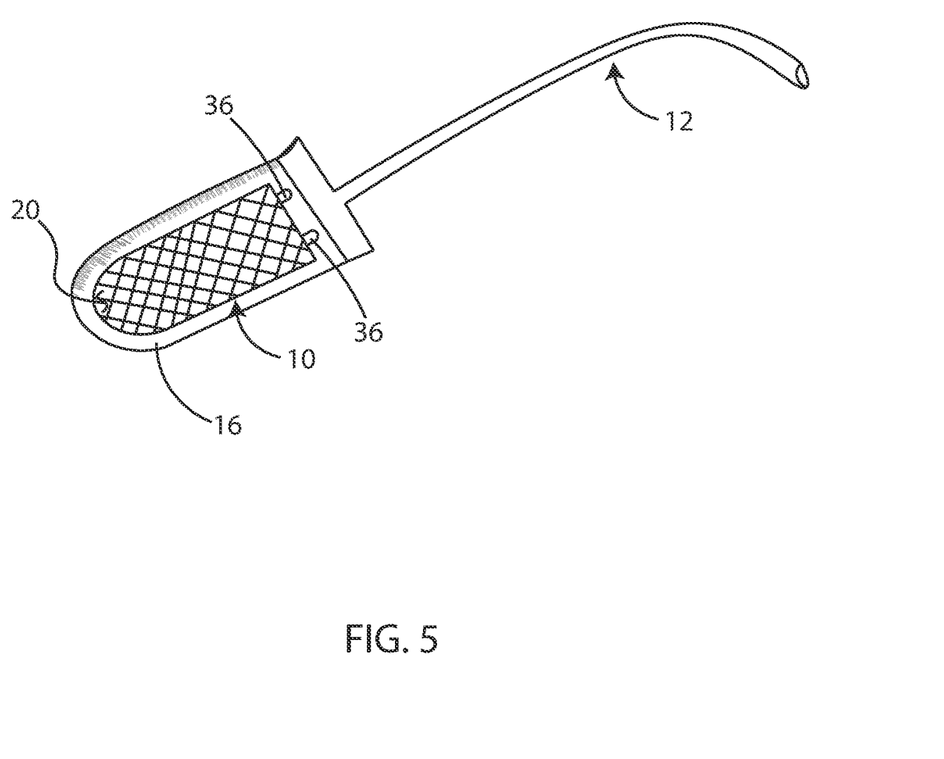
FIG. 5 is an illustration of the texturized oral device wherein the slip resistant patch further includes dead-end tabs.

As best shown in FIGS. 1 and 3, the adhesive material 26 is configured to temporarily adhere to at least one surface of an existing oral device 12, for example the tongue bulb 16, after removing a temporary film (not shown) from an adhesive surface of the adhesive material. As one would understand, a removable temporary film can be provided to cover the adhesive surface to prevent the adhesive surface from adhering to any unwanted substrates. In the preferred embodiment, the adhesive material 26 can be any pressure sensitive adhesive with hydrophobic/waterproof properties such as acrylates (e.g., methacrylates and epoxy diacrylates). As one would understand, alternative adhesives can be used in the scope of the present disclosure. Further, in order to separate the adhesive surface from the surface of an existing oral device 12, such as the tongue bulb 16, the slip-resistant patch 10 can include dead-end tabs 36 that can extend from a portion of the planar body 20 such that the dead-end tabs provide leverage for peeling the slip-resistant patch from the existing oral device, as shown in FIG. 5.

Figure 6:
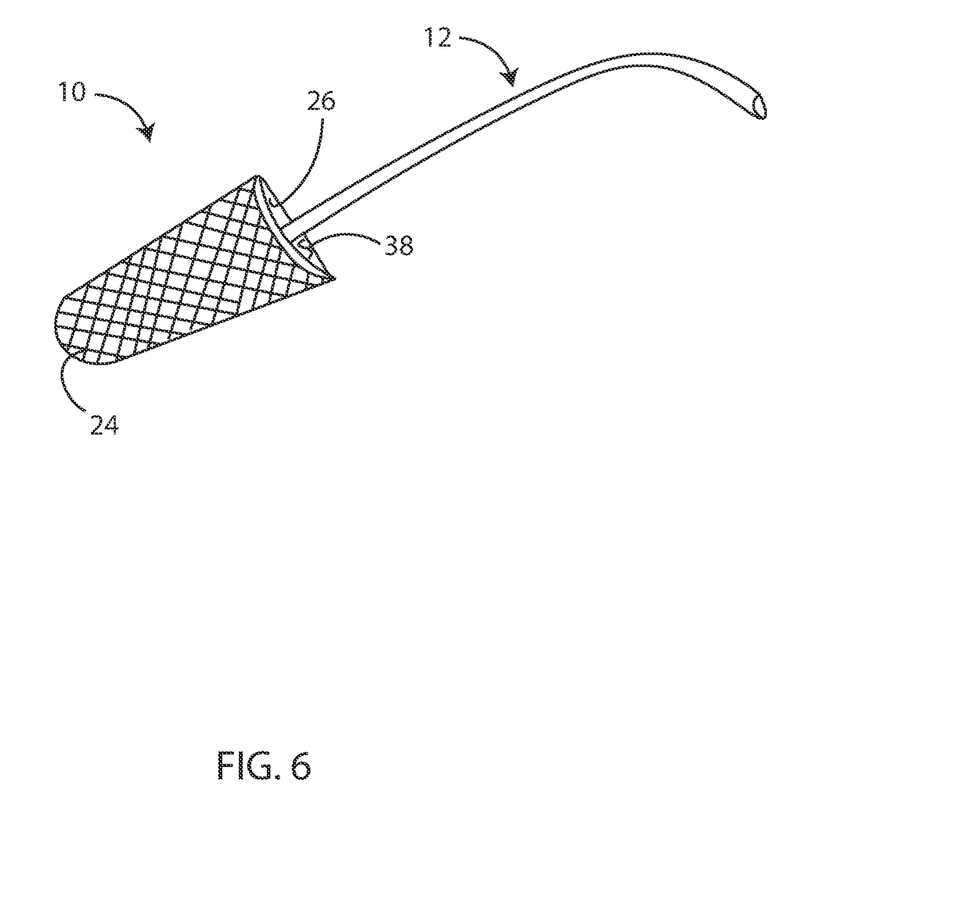
FIG. 6 is an illustration of a further alternative embodiment of the slip-resistant patch.

In alternative embodiments of the present disclosure, the slip-resistant patch 10 can be in a pouch-like patch, as shown in FIG. 6, or alternatively a sleeve-like patch (not shown), that can allow the existing oral device 12 to slide into a receiving area 38 of a pouch. The adhesive material 26 can be on at least one interior surface of the slip-resistant patch 10 while the textured material 24 is on at least one external surface of the slip-resistant patch such that the adhesive material affixes the existing oral device 12 within the pouch of the slip-resistant patch 10 and the textured material contacts a surface within an oral cavity. In this embodiment, a portion of the existing oral device 12, is encompassed by the slip-resistant patch 10. One would appreciate that an opening of a sleeve or the pouch of the slip-resistant patch 10 can be configured to allow the existing oral device 12 to be inserted into the receiving area 38 without contacting an adhesive surface of the adhesive material 26. Once the surface of the existing oral device 12 is fully inserted through the receiving area 38, the adhesive surface of the slip-resistant patch 10 can be adhered to the surface of the existing oral device by contact with the adhesive material 26.

Figure 7:
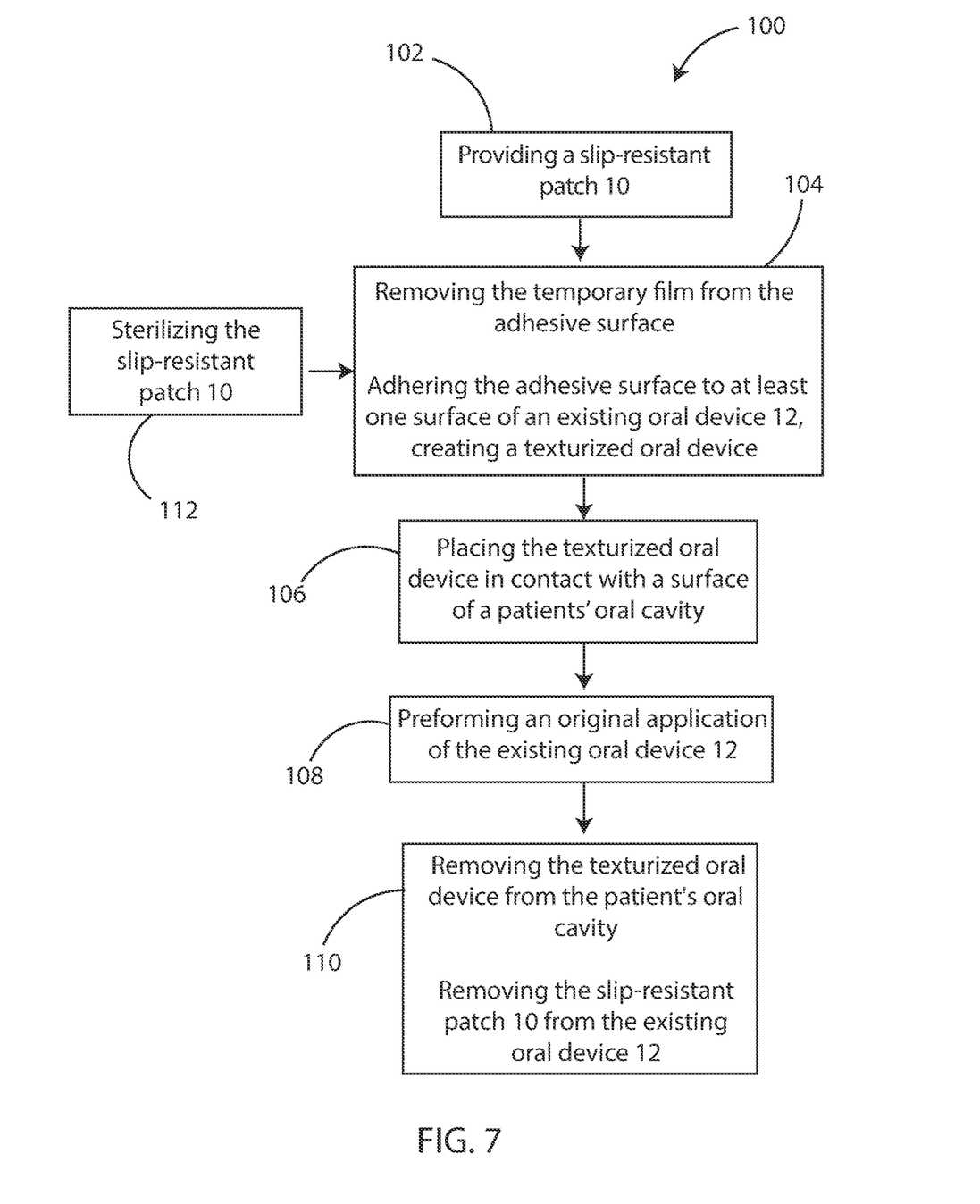
FIG. 7 is a schematic illustration of a method to reduce slippage of a tongue bulb.

Referring to FIG. 7, a method 100 to reduce slippage of an existing oral device 12 will now be briefly described. The method 100 comprises a step 102 of providing a slip-resistant patch 10 that includes a textured material 24, an adhesive material 26, and a temporary film covering an adhesive surface of the adhesive material. Further, step 104 includes removing the temporary film from the adhesive surface and temporarily adhering the adhesive surface to at least one surface of an existing oral device 12, creating a texturized oral device. In more detail, the slip-resistant patch 10 is positioned with the adhesive surface adjacent the surface of the existing oral device 12, such that the slip-resistant patch covers at least a portion of the surface and now outwardly presents a textured surface of the textured material 24 for contacting with at least a portion of the patient's oral cavity when the texturized oral device is positioned within the oral cavity. Step 106 involves placing the texturized oral device in contact with a surface of a patients' oral cavity by placing the textured surface in contact with the surface of the patients' oral cavity. Step 108 includes preforming an original application of the existing oral device 12, for example measuring tongue muscle performance, and the like. The method 100 can further include Step 110 of removing the texturized oral device from the patient's oral cavity by peeling away the slip-resistant patch 10 from the existing oral device. Peeling away the slip-resistant patch 10 from the existing oral device 12 can be accomplished with at least one dead-end tab 36 extending from a portion of a planar body 20 of the slip-resistant patch 10. In a general aspect of the present disclosure, the method can further include step 112 of sterilizing the slip-resistant patch 10 such that the slip-resistant patch is free of contaminates that can elicit at least one undesirable response in an oral cavity prior to placing in contact a surface of the existing oral device and a surface of a patients' oral cavity. Undesirable responses can include toxic, irritating, distasteful, inflammatory, harmful, or lethal effects, which would result in a product that is not biocompatible. Further in order to prevent undesirable responses an unused slip-resistant patch 10 is discarded after each use and a fresh slip-resistant patch is used for a new patient.

In the present disclosure the term 'slippage' is used to describe the movement of an oral device within an oral cavity, such as sliding around on the patient's tongue. Further, 'slippage' is primarily useful in characterizing unwanted or undesirable movement of the oral device within the oral cavity. Therefore, slippage of an oral device is movement that leads to inability, difficulty, or hindrance in using an oral device for an intended purpose or application. Further, an existing oral device 12, as best shown in FIG. 1, can alternatively be an oral device used for a variety of applications, including but not limiting to evaluation, diagnostic, therapeutic, preventative, rehabilitation, or assistive application within an oral cavity. The existing oral device 12 can be useful and beneficial across several clinical based fields, such as speech pathology, respiratory therapy, orofacial myofunctional therapy, dentistry, and orthodontics, along with research based fields, such as neuromuscular sciences and disorders, exercise science, biomedical engineering, and communication sciences and disorders. These practices help address functional and physiological lingual performance that are useful within a diverse scope of daily living features, such as swallowing, upper airway patency, articulation, pressure, strength, and endurance. Although the disclosed embodiments are illustrated and described herein as embodied in one or more specific examples, it is nevertheless not intended to be limited to the details shown, since various modifications and structural changes may be made without departing from the scope of inventions and within the scope and range of equivalents of the claims. In addition, various features from one embodiment may be incorporated into another of the embodiments. Accordingly, it is appropriate that the appended claims be construed broadly and, in a manner, consistent with the scope of the disclosure as set forth in the following claims.

The foregoing description has been presented for the purposes of illustration and description. It is not intended to be exhaustive or to limit the disclosure to the precise form disclosed. Many modifications and variations are possible in view of this disclosure. Indeed, while certain features of this disclosure have been shown, described and/or claimed, it is not intended to be limited to the details above, since it will be understood that various omissions, modifications, substitutions and changes in the apparatuses, forms, method, steps and system illustrated and in its operation can be made by those skilled in the art without departing in any way from the spirit of the present disclosure.

Furthermore, the foregoing description, for purposes of explanation, used specific nomenclature to provide a thorough understanding of the disclosure. However, it will be apparent to one skilled in the art that the specific details are not required in order to practice the disclosure. Thus, the foregoing descriptions of specific embodiments of the present disclosure are presented for purposes of illustration and description. They are not intended to be exhaustive or to limit the disclosure to the precise forms disclosed, many modifications and variations are possible in view of the above teachings. The embodiments were chosen and described in order to best explain the principles of the disclosure and its practical applications, to thereby enable others skilled in the art to best utilize the disclosed system and method, and various embodiments with various modifications as are suited to the particular use contemplated.

What is claimed is:

1. A slip-resistant patch for a tongue bulb, the slip resistant patch comprising:
   a perimeter portion, the perimeter portion defining a shape and size of the slip-resistant patch;
   a planar body defined by the perimeter portion of the slip-resistant patch, the planar body being configured to contour to a surface of the tongue bulb, the planar body comprising a first major surface and an opposing second major surface, wherein the first major surface comprises a textured material and the second major surface comprises an adhesive material, the textured material being configured to be positioned on a surface of an oral cavity and maintain position on the surface of the oral cavity throughout lingual movement within the oral cavity, the adhesive material being of a pressure sensitive material and being configured to adhere to the surface of the tongue bulb.

2. The slip-resistant patch of claim 1, further comprising a punch or sleeve configured to receive the tongue bulb, such that at least a portion of the tongue bulb is encompassed within the pouch or sleeve.

3. The slip-resistant patch of claim 1, wherein the slip-resistant patch is sterilized to be free of contaminates capable of eliciting an undesirable response in an oral cavity, wherein the undesirable response includes at least one of toxic, irritating, distasteful, inflammatory, harmful, and lethal effects.

4. The slip-resistant patch of claim 1, wherein the textured material is at least one material selected from fabric, cloth, fiber, and any combination thereof, and wherein the textured material is of synthetic and/or natural origins.

5. The slip-resistant patch of claim 1, wherein the tongue bulb is a device for at least one of evaluation, diagnostic, therapeutic, prevention, rehabilitation, and assistive applications.

6. The slip-resistant patch of claim 1, wherein the tongue bulb includes at least one air-filled bulb.

7. The slip-resistant patch of claim 1, wherein the shape defined by the perimeter portion of the slip-resistant patch is at least one geometry selected from circular, oblong, square, rectangular, pentagonal, hexagonal, and any combination thereof.

8. The slip-resistant patch of claim 1, wherein the size defined by the perimeter portion of the slip-resistant patch covers at least half of at least one surface of the tongue bulb.

9. The slip-resistant patch of claim 1, further comprising at least one dead end tab extending from a portion of the planar body along the perimeter portion, wherein the at least one dead end tab is configured to provide leverage for peeling the adhesive material from the surface of the tongue bulb.

10. A method to reduce slippage of a tongue bulb comprising:
    providing the slip-resistant patch of claim 1;
    adhering the adhesive material to at least one surface of the tongue bulb, creating a texturized tongue bulb; and
    placing the texturized tongue bulb in contact with at least one surface of a patient's oral cavity.

11. The method of claim 10, wherein placing the texturized tongue bulb in contact with at least one surface of the patient's oral cavity comprises placing the texturized tongue bulb in contact with at least one of the patient's tongue, lips, hard palate, cheeks, gums, teeth, and mouth floor.

12. The method of claim 10, further comprising using the texturized tongue bulb for at least one of evaluation, diagnostic, therapeutic, preventative, rehabilitation, and assistive applications.

13. The method of claim 10, wherein the textured material is configured for at least one of reducing oral device slippage inside an oral cavity, ensuring optimal placement of the oral device, and providing a patient an ability to keep an oral device in an intended general position.

14. The method of claim 10, further comprising removing the texturized tongue bulb from the patient's oral cavity; and removing the slip-resistant patch from the tongue bulb by peeling said patch away from said at least one surface of the tongue bulb.

* * * * *